United States Patent [19]

Holmes et al.

[11] 4,350,511
[45] Sep. 21, 1982

[54] DISTILLATIVE SEPARATION OF CARBON DIOXIDE FROM LIGHT HYDROCARBONS

[75] Inventors: Arthur S. Holmes, Shrewsbury; James M. Ryan, Weston, both of Mass.

[73] Assignee: Koch Process Systems, Inc., Westboro, Mass.

[21] Appl. No.: 306,419

[22] Filed: Sep. 28, 1981

Related U.S. Application Data

[63] Continuation-in-part of Ser. No. 131,416, Mar. 18, 1980, abandoned.

[51] Int. Cl.³ ............................................... F25J 3/04
[52] U.S. Cl. .......................................... 62/17; 62/20; 62/28; 55/68
[58] Field of Search .................... 62/17, 20, 23–28; 55/68

[56] References Cited

U.S. PATENT DOCUMENTS

| | | | |
|---|---|---|---|
| 3,130,026 | 4/1964 | Becker | 62/17 |
| 3,595,782 | 7/1971 | Bucklin et al. | 62/23 |
| 4,012,212 | 3/1977 | Kniel | 62/17 |
| 4,035,167 | 7/1977 | Starks | 62/17 |
| 4,185,978 | 1/1980 | McGalliard | 62/23 |
| 4,311,495 | 1/1982 | Styring, Jr. | 62/28 |

FOREIGN PATENT DOCUMENTS

1033952  7/1978  Canada .

Primary Examiner—Norman Yudkoff
Attorney, Agent, or Firm—Richard P. Crowley

[57] ABSTRACT

An improved distillative separation of carbon dioxide and light hydrocarbons is disclosed in which the formation of an azeotrope between these components is prevented by addition of an agent to said distillation column and in which prevention of the azeotrope allows a more complete separation to be achieved.

24 Claims, 7 Drawing Figures

DISTILLATIVE SEPARATION OF CARBON DIOXIDE FROM LIGHT HYDROCARBONS

REFERENCE TO PRIOR APPLICATION

This application is a continuation-in-part of U.S. Ser. No. 131,416, filed Mar. 18, 1980 (now abandoned).

TECHNICAL FIELD

This invention is in the field of distillation.

BACKGROUND ART

It is often desirable to separate carbon dioxide components from light hydrocarbons in the processing of gas streams. Certain of these separations are, however, made difficult because of the tendency of mixtures of light hydrocarbons and acid gases to form azeotropes.

One such example can be found in the cryogenic distillative separation of methane from acid gas components described in our copending application, Ser. No. 94,226, filed Nov. 14, 1979. This process is particularly effective for separating methane from high $CO_2$-content feed in one distillation column without solids formation. The bottoms product of this process contains carbon dioxide, ethane, and higher hydrocarbons, and it is often desirable to separate the carbon dioxide and ethane components in this bottoms product. Such a separation would produce a useful carbon dioxide product as well as an enriched ethane product which could be used for its heating value or as raw material in many chemical syntheses.

Although highly desirable, the separation of carbon dioxide from ethane by distillation has proven to be a difficult problem in practice. This difficulty is caused by the fact that carbon dioxide and ethane form an azeotrope of approximately two thirds carbon dioxide and one third ethane on a mole basis. For a feed mixture containing ethane and carbon dioxide, this azeotrope tends to form in the upper portion of the column, usually making further separation beyond the azeotrope composition impossible. The common practice of employing two distillation towers operating at different pressures to work around the azeotrope does not help with the carbon dioxide/ethane system because pressure has only minimal effect on the composition of the azeotrope. Because of this, attempts to separate carbon dioxide from ethane by distillation have heretofore resulted in an overhead carbon dioxide stream containing approximately azeotropic amounts of ethane, which are unacceptable in many applicatons.

Ethylene also forms an azeotrope with carbon dioxide. Additionally, it is known that the acid gas hydrogen sulfide forms azeotropes with both ethane and propane. These and other possible azeotropes between acid gases and light hydrocarbons present limitations similar to those described for the carbon dioxide/ethane system when efforts are made to perform distillative separations on such systems.

DISCLOSURE OF THE INVENTION

This invention relates to the distillative separation of acid gases from light hydrocarbons in mixtures wherein such separations are normally limited by the tendency to form an azeotrope. The feed mixtures can, of course, contain additional components such as higher hydrocarbons, nitrogen, hydrogen, etc.

In the method of this invention, a distillation column can be used to separate an acid gas and light hydrocarbon, both present in the feed, into an overhead and bottoms product which are not limited by the azeotrope composition of the acid gas or light hydrocarbon. This is achieved by adding to the distillation column an agent which prevents formation of the acid gas/light hydrocarbon azeotrope. For example, an agent which prevents azeotrope formation can be employed in the distillative separation of a binary of carbon dioxide and ethane to produce an overhead stream having significantly more than two thirds carbon dioxide, which is the limitation when an azeotrope forms.

In addition to obtaining a purer overhead product, this method has other inherent advantages. In many instances, for example, the energy requirements are lower than in the corresponding separation without agent because the relative volatility is improved or because the separation can be made at higher temperatures. This, of course, can lower the cost for the separation.

Sometimes materials capable of eliminating azeotropes are contained in the feed mixtures. For example, natural gas typically contains butane, which can be an effective agent for preventing azeotrope formation between carbon dioxide and ethane. Although the mere presence of such materials in the feed is not sufficient to prevent azeotrope formation, such materials can be separated from bottoms product and added back to the column at an appropriate point to prevent azeotrope formation. This takes advantage of materials already present in the feed as a convenient source of agents.

BEST MODE OF CARRYING OUT THE INVENTION

This invention will now be further described in more specific detail with regard to the figures.

Much of the data presented in the following description, as well as that shown in the Figures, was obtained using a plate-to-plate column calculation program to simulate conditions within a distillation column for certain given or desired operating conditions. Unless otherwise stated, the program employed was the Process Simulation Program of Simulation Sciences, Inc., Fullerton, Calif., Oct.–Nov. 1979. Vapor-liquid equilibria and thermodynamic data were calculated based upon the Soave-Redlich-Kwong equation of state. While the total accuracy of the data obtained cannot be assured, and in fact will change somewhat depending upon the constants chosen, the data is believed to be representative of actual data and is certainly appropriate for illustrating and substantiating the benefits gained by use of an agent to prevent azeotrope formation in distillative separations of an acid gas from a light hydrocarbon according to this invention. For purposes of simplifying the plots, data from systems which were not binary were plotted on a pseudo-binary basis in which mole fractions are calculated as if the components beyond those in the binary were not present.

Figure 1:
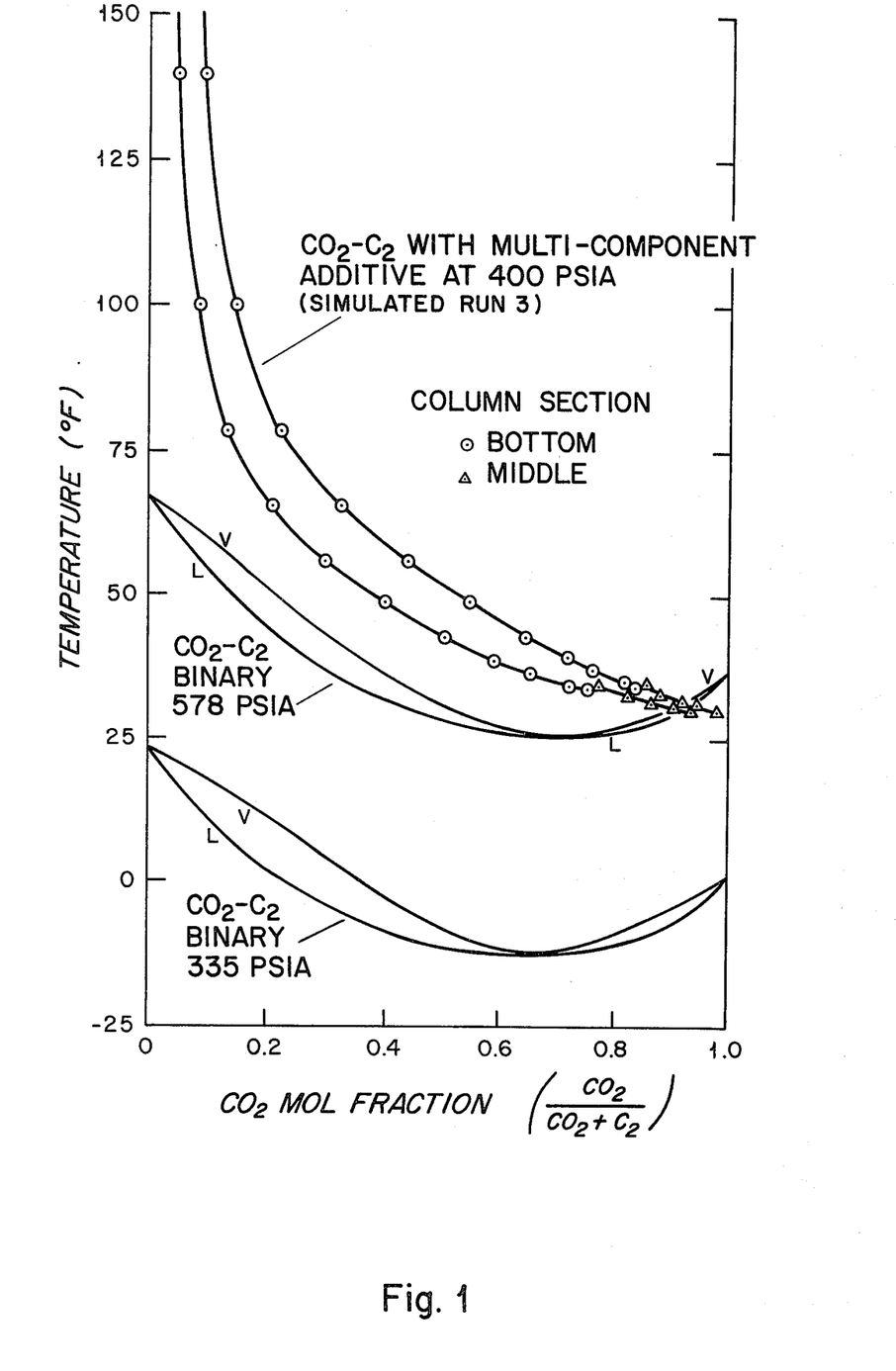
FIG. 1 is a plot of vapor-liquid equilibria data for a binary system of carbon dioxide and ethane at two different pressures, as well as data from a computer simulated separation illustrating the effect on such a system of the addition of an agent for preventing azeotrope formation.

The practical difficulty of obtaining a complete separation of carbon dioxide from ethane in a gas mixture containing both can be seen by referring to Figure 1. FIG. 1 contains vapor-liquid equilibria data for a binary mixture of carbon dioxide and ethane at both 578 psia and 335 psia. Data for these binary mixtures were obtained by Arthur D. Little, Inc. using an inhouse computer program and employing the Soave-Redlich-Kwong equation of state. As can be seen from the data, the binary mixtures form a minimum boiling point azeotrope at both pressures in the range of about 65–70% carbon dioxide. Thus, a mixture of carbon dioxide and ethane tends toward the azeotropic composition as the gas rises up the distillation column. Once the azeotrope composition is reached, further separation of the binary does not occur. Thus, the overhead product typically contains the azeotropic amount of ethane, which in this case would amount to approximately one third of the overhead product, on a mole basis. The data also demonstrate that the effect of pressure on composition of an azeotrope in this system is minimal, meaning that the use of two distillation columns operating at different pressures is not a viable solution to the problem.

The beneficial effect of adding an agent to eliminate the azeotrope is demonstrated in the upper plot of vapor-liquid equilibria data for carbon dioxide and ethane, but additionally including a mixture of $C_3$–$C_6$ alkanes, which together function as an additive to prevent azeotrope formation between carbon dioxide and ethane. The exact compositions and operating conditions are discussed in more detail below with reference to Simulated Run 3.

It can be seen from the data plotted that the azeotrope has been eliminated in the simulated run with additive. Thus, further separation of carbon dioxide and ethane, beyond the azeotrope amounts of the binary, can be achieved.

Figure 2:
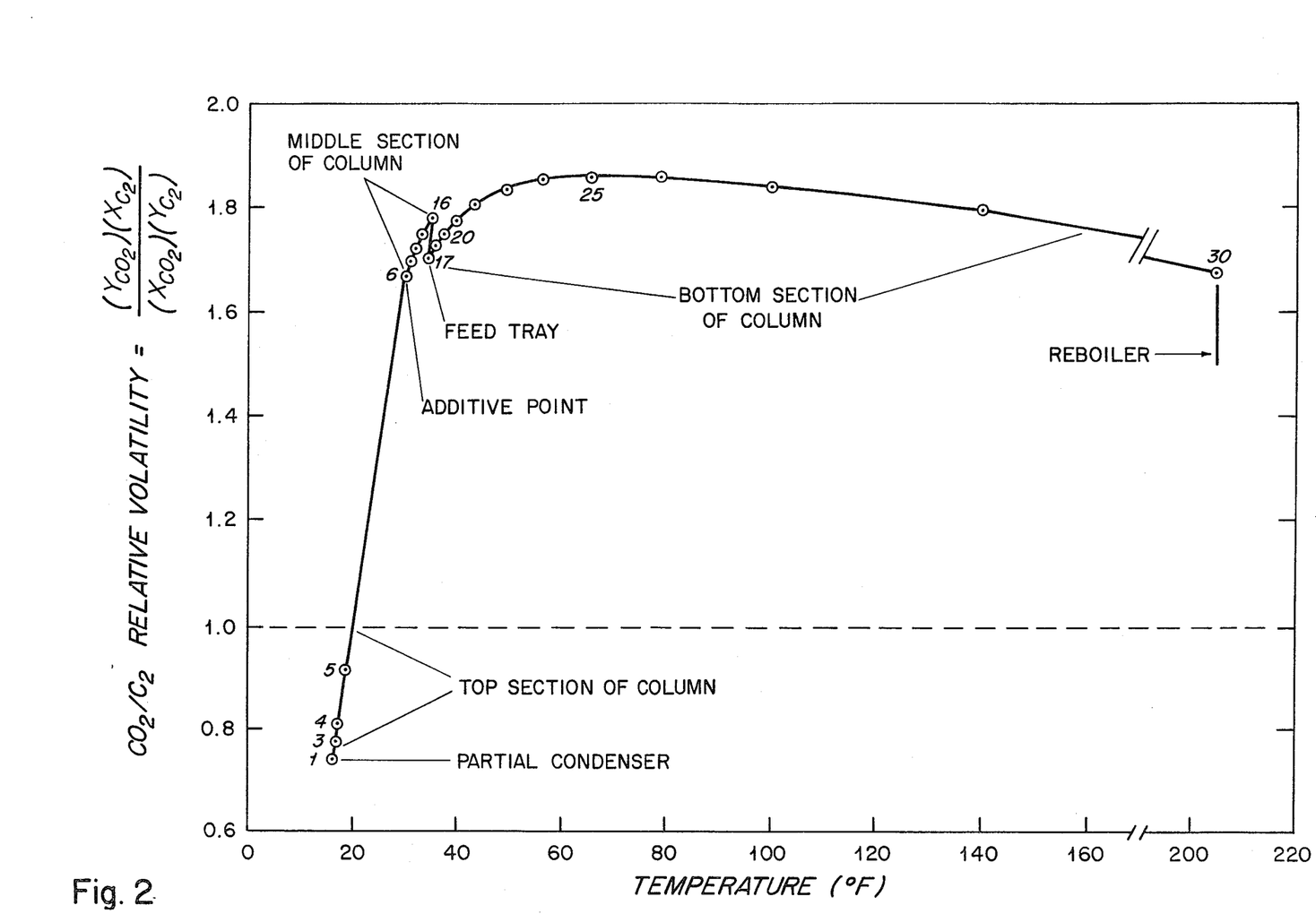
FIG. 2 is a plot of the relative volatility of carbon dioxide to ethane at various temperatures in a computer simulated distillation having a multi-component hydrocarbon mixture added to serve as an agent for preventing azeotrope formation.

The beneficial effect of the additive is also dramatically demonstrated by the data regarding the relative volatility of carbon dioxide to ethane which is plotted in FIG. 2. As seen in FIG. 2, the relative volatility is about 1.65 at the point in the column where the additive is introduced. It remains at or above this value at all points below the point of addition, which comprise the middle and bottom sections of the column. In the top section of the column, above the additive addition point, the relative volatility slips to values below 1, indicating that ethane is actually more volatile than carbon dioxide in the top section of the column above where the additive was introduced. Thus, efforts to recover the additive actually reverse the natural relative volatilities of these materials.

The beneficial effect of the additive in accomplishing a reversing of relative volatility of $CO_2$ relative to ethane is shown in FIG. 2, which data are from simulated Run 3 below. Although the feed is 60% $CO_2$, the overhead product from the partial condenser is 97.8% $CO_2$, which is well above the azeotrope concentration 65 to 70% $CO_2$ as shown in FIG. 1. The liquid flow from the partial condenser is 97.9% $CO_2$ and is approximately 0.7% $C_3+$. The volatility of $CO_2$ relative to $C_2$ is 0.74 which means that, with further distillation, the $CO_2$ purity relative to $C_2$ purity of an overhead vapor will actually decrease. Stages 5, 4, 3, 2 and 1, all of which are above the tray where liquid additive is introduced, have relative volatilities of less than 1.0. The ethane content of vapors proceeds from 1.6% in the vapor flow entering Stage 5 and rises to 1.8% in the overhead product vapor flow from the partial condenser.

Additive is fed into Stage 6 and is mainly present in the liquid. In Stage 6 additive, $C_3+$, concentration in the liquids is 32.7% and in the vapor 2.7%. The influence of additive can be seen by comparing Stage 5 and Stage 6. Additive in the liquid of Stage 5 is 6.02% and in Stage 6, 32.7%. In Stage 5, $CO_2$ in the vapor is 97% and in Stage 6, 96%. The result of the substantial concentration of additive in Stage 6 is to give a relative volatility of 1.66, while, with insufficient additive in Stage 5, the relative volatility is 0.90.

Additive $C_3+$ possesses limited volatility. The function of Stages 1, 2, 3, 4 and 5 is to knock back additive and prevent it from being coproduced in the $CO_2$ overhead product. The knocking back succeeds, and $C_3+$ in the vapor of Stage 6 is 2.7%, Stage 5 1.5%, Stage 4 0.99% and successively lower values with 0.36% in the overhead product.

Starting with the stage where additive is fed in and on down to the column bottom, additive is present in the liquid at levels of greater than 30%. In every stage at or below the additive point, the relative volatility of $CO_2$ relative to $C_2$ is greater than 1.0, meaning that proceeding downward, $CO_2$ is depleted relative to $C_2$ which is concentrated. The bottom product contains 10.9 mols/hr. of $CO_2$ and 290 mols/hr. of $C_2$, practically complete elimination of $CO_2$, while 93.5% of the $C_2$ fed into the column is produced in the bottoms product flow. The amount of additive, $C_3+$, in the liquids in the section of the column above the feed tray up to the additive tray is between 32 and 34%, giving rise to relative volatility of $CO_2$ relative to $C_2$ of 1.65 to 1.80. From the feed tray down, the additive concentrations in the liquids are, from tray 17 to 24, relatively constant, 31 to 34%. The additive concentrations rise in the lowest trays where the temperature rises; tray 25 has 39% and tray 30 has 82%.

In general, the amount of the liquid additive agent to be employed may vary, such as, for example, from about above 10% mol and above, for example, 20% and above in the column, and particularly 25% mol and above. The liquid additive agent may range in concentration in one embodiment from about 30 to 50% mol in the main zone of the column and be present in about 70 to 90% mol in the hydrocarbon-enriched bottoms product.

Figure 3:
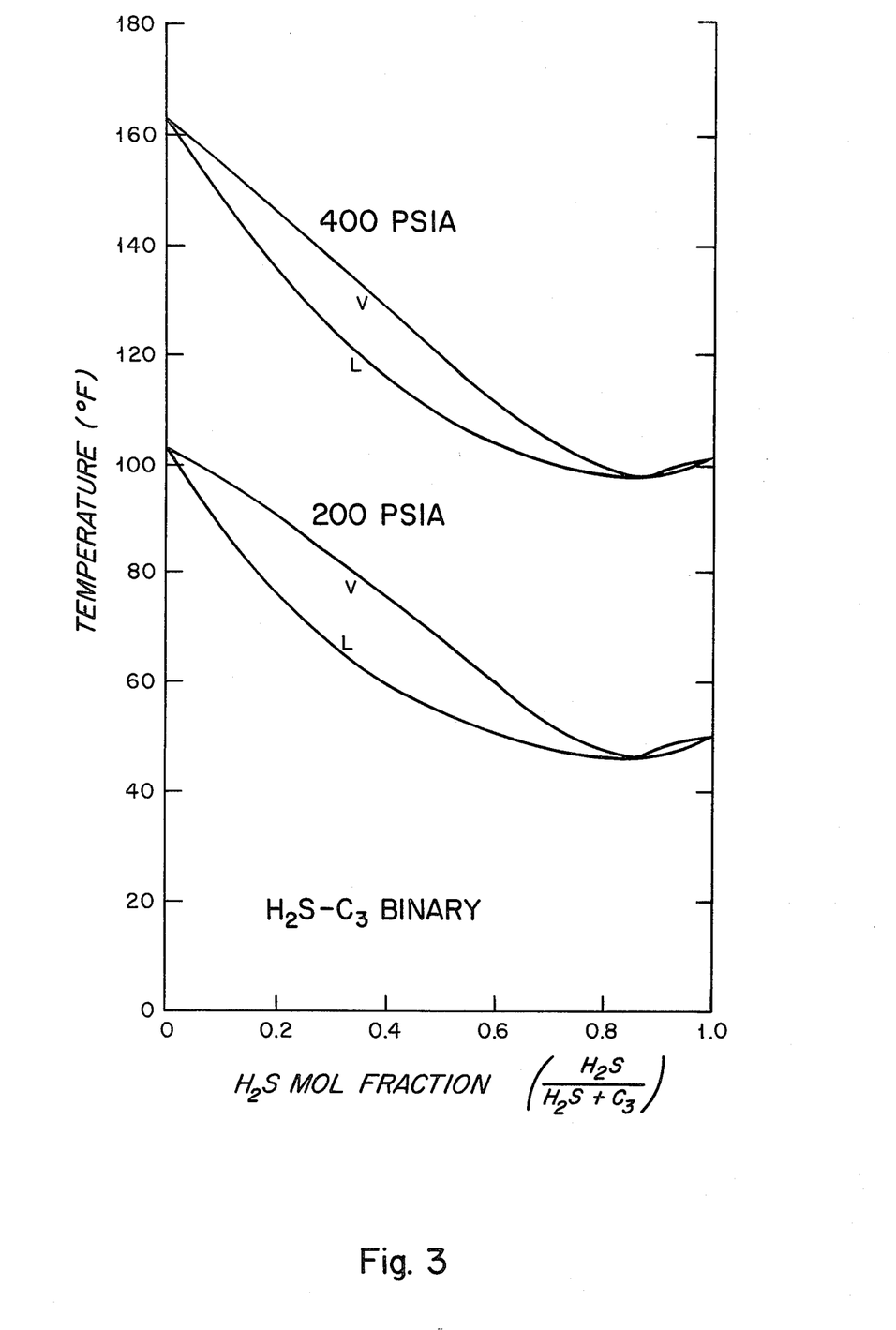
FIG. 3 is a plot of vapor-liquid equilibria data for a binary system of hydrogen sulfide and propane at 200 and 400 psia.

FIG. 3 is a plot of vapor-liquid equilibria data for a binary system of hydrogen sulfide and propane. In a manner similar to the binary system of carbon dioxide and ethane, the hydrogen sulfide/propane system exhibits azeotrope formation at both 200 and 400 psia. Although the azeotrope occurs at a somewhat higher mole fraction of hydrogen sulfide; e.g., 84–85 mole percent, nevertheless the azeotrope formation does interfere with a more complete distillative separation.

Figure 4:
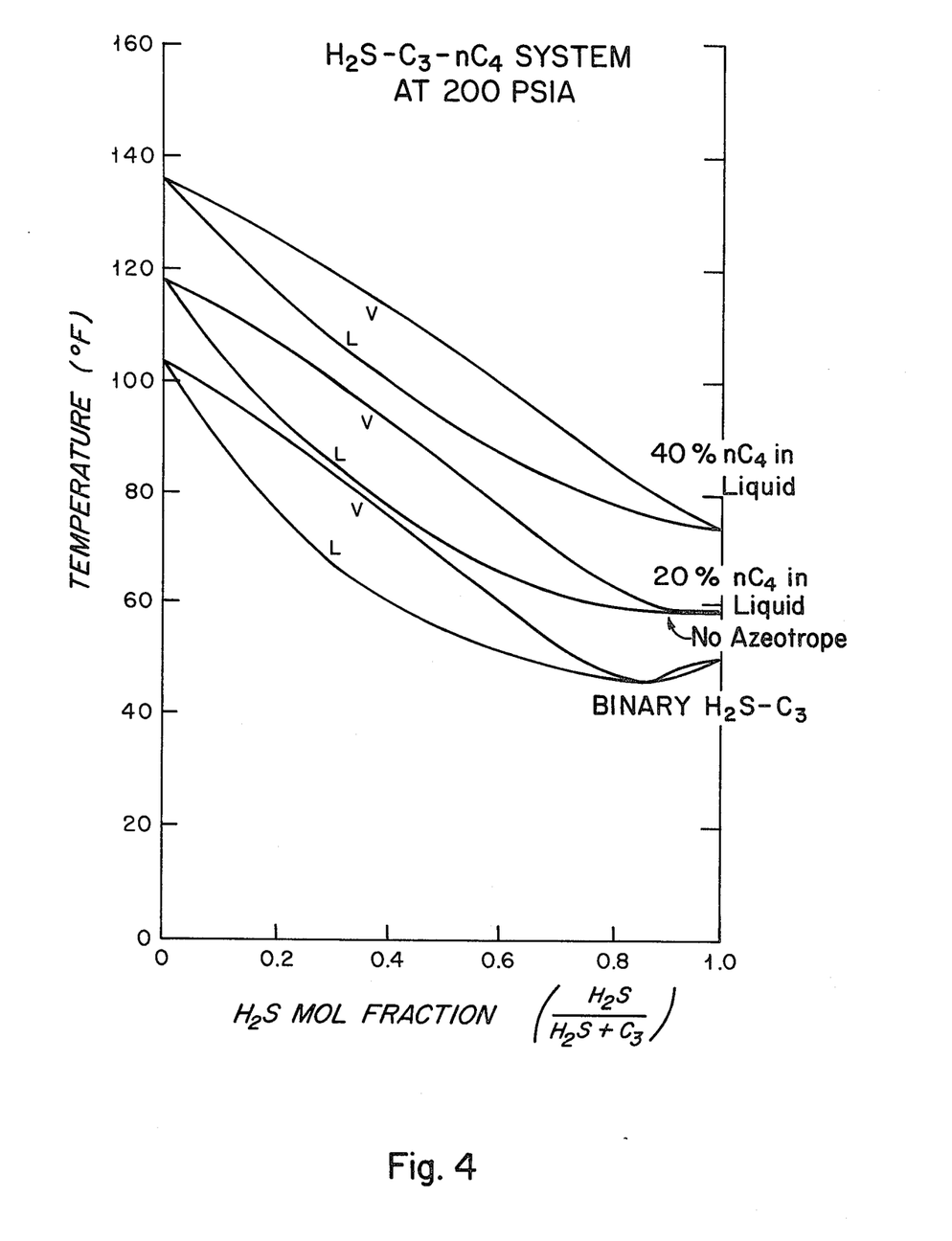
FIG. 4 is a plot of vapor-liquid equilibria data at 200 psia for the hydrogen sulfide/propane system containing 0, 20 and 40% butane in the liquid phase.

FIG. 4 presents vapor-liquid equilibria data for a binary hydrogen sulfide/propane system, as well as this system with n-butane added to prevent azeotrope formation between hydrogen sulfide and propane. It can be seen that the azeotrope illustrated in FIGS. 3 and 4, which occurs at 200 psia for the pure binary, is eliminated by the addition of n-butane to a level of 20%. The pinched portion of the vapor-liquid eqilibrium plot is opened even more when n-butane is added to a level of 40%. Thus, in addition to eliminating the azeotrope, the n-butane additive also increases the relative volatility of hydrogen sulfide to propane near the azeotrope composition. Further, the addition of n-butane also increases the column temperatures, which lowers the energy requirements for refrigeration. Because of these factors, it might be desirable to add n-butane to hydrogen sulfide/propane systems even though the separation will not be extended beyond the azeotrope composition.

Figure 5:
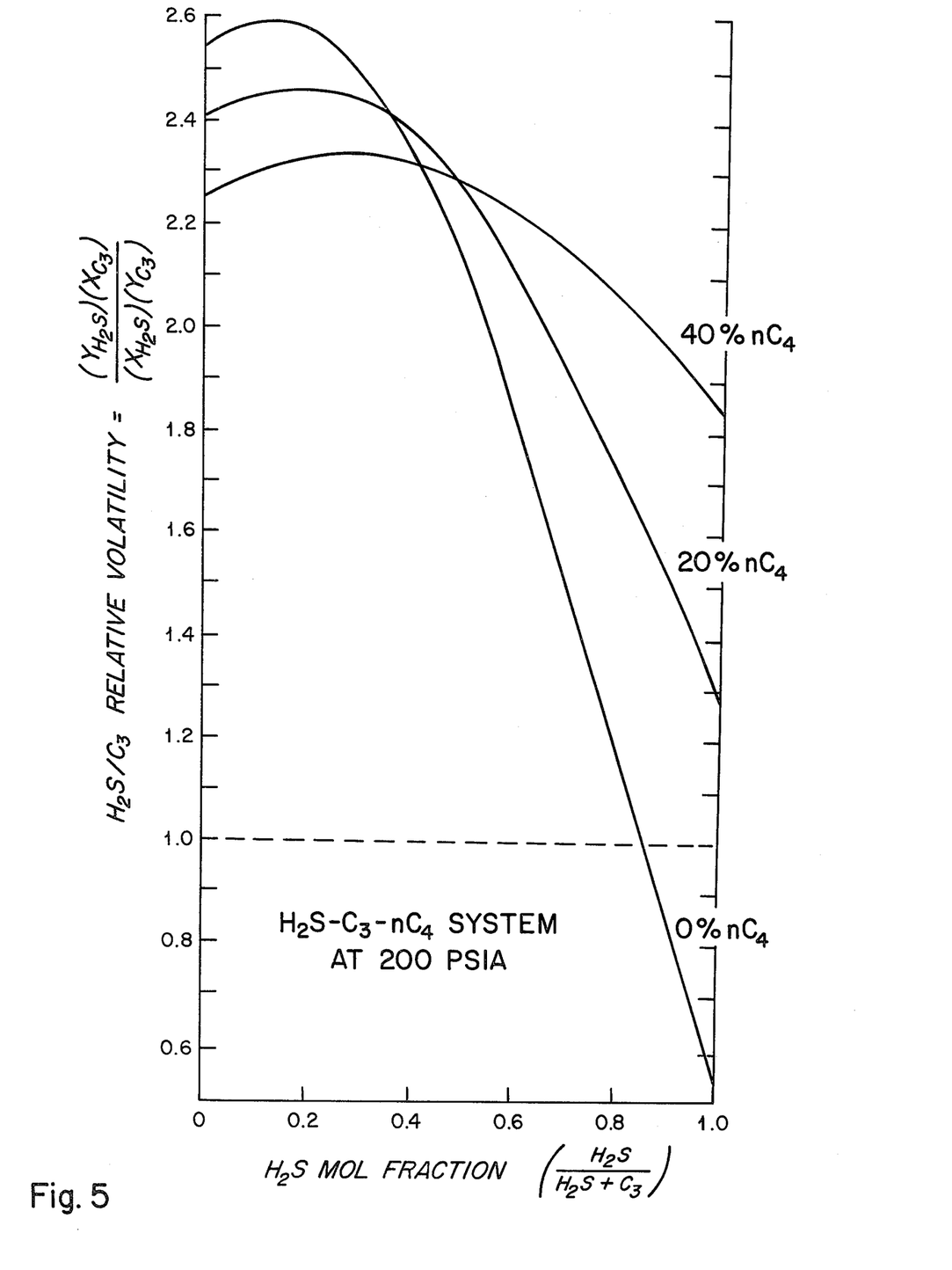
FIG. 5 is a plot of the relative volatility of hydrogen sulfide to propane in systems containing 0, 20 and 40% butane in the liquid phase, plotted against liquid phase composition.

FIG. 5 is a plot of the relative volatility of hydrogen sulfide to propane, with and without n-butane as an additive. As illustrated, with no additive, the relative volatility falls below 1 for mole percentages of hydrogen sulfide above about 84%. Addition of n-butane raises the relative volatility well above 1, even for the higher percentages of hydrogen sulfide. Thus, as noted above, it can be desirable to add agent to enhance relative volatility even below the azeotrope composition, as illustrated.

Figure 6:
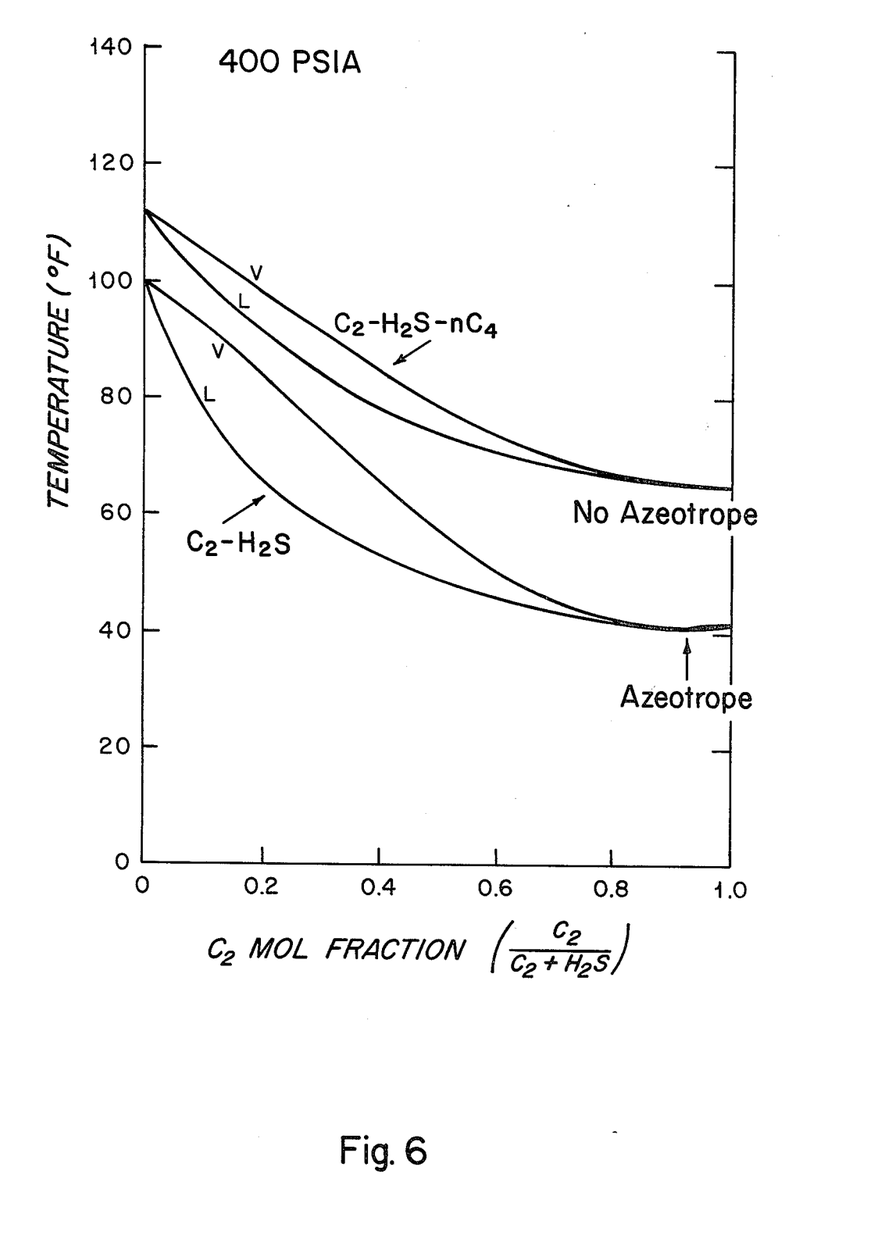
FIG. 6 is a plot of vapor-liquid equilibria for a binary system of hydrogen sulfide and ethane as well as data illustrating the effect of the addition of butane to this system to prevent azeotrope formation.

FIG. 6 is a plot of vapor-liquid equilibria data for the binary hydrogen sulfide/ethane system and for this system with n-butane at a level of 20% added to the liquid phase. In this system, the light hydrocarbon ethane is more volatile than the acid gas hydrogen sulfide below the azeotrope. As can be seen, the azeotrope present in the binary is eliminated by the addition of n-butane to a level of 20%.

In order to further describe this invention, the results of three distillations simulated on a computer will now be presented.

SIMULATED RUN 1

Summary

| | |
|---|---|
| Feed, Mols[e]/Hr. | 1646 |
| Feed $CO_2$, Mol % | 65 |
| Feed Ethane, Mol % | 9.9 |
| Stages[a], Total | 20 |
| Additive Rate, Mols/Hr | 986.3 |
| Ethane Recovery in Bottoms Product, % | 64.7 |
| Ethane Composition in Overhead, Mol % | 5.3 |
| $CO_2$ Recovery in Overhead, % | 96.8 |
| Additive Loss Into Overhead, Mols/Hr | 2.5 |
| "Split", $\dfrac{(CO_2 \text{ Ohd}) (\text{Ethane Btm})}{(CO_2 \text{ Btm}) (\text{Ethane Ohd})}$ | 52.9 |

Column Operation - 500 psia

| Heating (Cooling) Duty MMBTU/Hr | | Temperature | Location Stage | |
|---|---|---|---|---|
| b | c | | | |
| (4.8) | (2.9) | 30° F. | 1 | Overhead Partial Condenser |
| — | — | — | 2 thru 5 | Top Section of Column |
| — | — | 98° F. | 6 | Additive Fed In |
| — | — | — | 7 thru 11 | Middle Section of Column |
| — | — | 68° F. | 12 | Feed |
| — | — | — | 13 thru 19 | Bottom Section of Column |
| 18.5 | 11.2 | 251° F. | 20 | Reboiler |

Material Balance

| | Feed | Additive | Overhead | Bottoms | |
|---|---|---|---|---|---|
| Mols/Hr $CO_2$ | 1072.3 | 1.0 | 1038.0 | 35.3 | 96.8% Recovery in Overhead |
| Mols/Hr Ethane | 163.5 | 1.0 | 58.7 | 105.8 | 64.7% Recovery in Bottoms |
| Mols/Hr Propane | 142.2 | 1.0 | .2 | 143.0 | |
| Mols/Hr n-Butane | 268.5 | 983.3 | 2.3 | 1249.5 | |
| TOTAL | 1646.5 | 986.3 | 1099.2 | 1533.6 | |
| Mol % $CO_2$ | 65.1 | 0.1 | 94.4 | 2.3 | |
| Mol % Ethane | 9.93 | 0.1 | 5.3 | 6.9 | |
| Mol % Propane-Plus | 25.0 | 99.8 | 0.23 | 90.8 | |
| °F. Temperature | 62.9 | 88.0 | 30.3 | 251.4 | |
| Mol % Liquid | 100 | 100 | 0 | 100 | |
| Mol % $CO_2$ (Pseudo-bin.[d]) | 86.8 | — | 94.6 | 25.0 | |

Conditions at Selected Stages

| Stage Number | 1 | 6 | 12 | 20 |
|---|---|---|---|---|
| Temperature, °F. | 30.3 | 98.0 | 67.6 | 251 |
| Liquid, $CO_2$, Mol % | 94.7 | 35.6 | 46.7 | 2.30 |
| Liquid, Ethane, Mol % | 4.45 | 4.23 | 10.1 | 6.89 |
| Liquid, Propane-Plus, Mol % | 0.85 | 60.2 | 43.2 | 90.8 |
| Liquid, Reduced Temp. | 0.892 | 0.822 | 0.828 | 0.966 |
| Liquid Flow, Mols/Hr | 1100 | 2093 | 3634 | 1534 |

-continued

SIMULATED RUN 1

| | | | | |
|---|---|---|---|---|
| Vapor, $CO_2$, Mol % | 94.4 | 82.1 | 81.5 | 5.86 |
| Vapor, Ethane, Mol % | 5.34 | 5.34 | 10.4 | 12.8 |
| Vapor, Propane-Plus, Mol % | 0.23 | 12.6 | 8.1 | 81.3 |
| Vapor Flow, Mols/Hr | 1099 | 1803 | 2355 | 3510 |
| Relative Volatility, $CO_2$:Ethane | 0.831 | 1.83 | 1.69 | 1.37 |

[a] Stages are theoretical stages (trays, partial condensers, reboilers), 100% efficient.
b For full amount of feed, as shown.
c Per 1000 mols/hr. of feed

[d] Pseudo-binary $CO_2$ composition $= \left( \dfrac{CO_2}{CO_2 + \text{ethane}} \right) \times 100$

[e] Mols cited are lb-mols

SIMULATED RUN 2

Summary

| | |
|---|---|
| Feed, Mols[e]/Hr. | 9945 |
| Feed $CO_2$, Mol % | 32 |
| Feed Ethane, Mol % | 19 |
| Stages[a], Total | 25 |
| Additive Rate, Mols/Hr | 6087 |
| Ethane Recovery in Bottoms Product, % | 91.0 |
| Ethane Composition in Overhead, Mol % | 5.1 |
| $CO_2$ Recovery in Overhead, % | 95.9 |
| $H_2S$ elimination from overhead, % | 98.3 |
| Additive Loss Into Overhead, Mols/Hr | 7.8 |
| "Split", $\dfrac{(CO_2 \text{ Ohd})(\text{Ethane Btm})}{(CO_2 \text{ Btm})(\text{Ethane Ohd})}$ | 234 |

Column Operation - 400 psia

| Heating (Cooling) Duty MMBTU/Hr | | Temperature | Location Stage | |
|---|---|---|---|---|
| b | c | | | |
| (10.9) | (1.1) | 15° F. | 1 | Overhead Partial Condenser |
| | | | 2 thru 5 | Top Section of Column |
| (13.7) | (1.4) | 62° F. | 6 | Intermediate Partial Condenser |
| | | | | Additive Added to Stage 6 |
| | | | 7 thru 13 | Middle Section of Column |
| — | — | 80° F. | 14 | Feed Vapor Addition |
| — | — | 80° F. | 15 | Feed Liquid Addition |
| | | | 16 thru 24 | Bottom Section of Column |
| 94.0 | 9.4 | 210° F. | 25 | Reboiler |

Material Balance

| | Feed | Additive | $CO_2$ Product Overhead | Ethane-Plus Product Bottoms | |
|---|---|---|---|---|---|
| Mols/Hr Methane | 32.1 | 0.0 | 0.0 | 32.1 | |
| Mols/Hr $CO_2$ | 3189.8 | 0.0 | 3058.1 | 131.7 | 95.9% Recovery in Overhead |
| Mols/Hr Ethane | 1851.7 | 0.0 | 167.0 | 1684.7 | 91.0% Recovery in Bottoms |
| Mols/Hr $H_2S$ | .235 | 0.0 | .0040 | .231 | 98.3% Elimination From Overhead |
| Mols/Hr Propane | 1062.0 | 60.9 | 2.8 | 1084.1 | |
| Mols/Hr Butane-Plus | 3844.8 | 6025.7 | 5.0 | 9865.5 | |
| TOTAL | 9944.6 | 6086.6 | 3232.9 | 12798.3 | |
| Mol % $CO_2$ | 32.1 | 0.0 | 93.7 | 1.03 | |
| Mol % $C_2$ | 18.6 | 0.0 | 5.11 | 13.2 | |
| Mol % Propane-Plus | 49.0 | 100.0 | .24 | 85.8 | |
| ppm $H_2S$ | 23.6 | 0.0 | 1.22 | 18.1 | |
| °F. Temp | 75.8 | 57.0 | 14.8 | 209.5 | |
| Mol % Liquid | 83.6 | 100.0 | 0.0 | 100.0 | |
| Mol % $CO_2$ (pseudo-bin.[d]) | 63.3 | — | 94.8 | 7.3 | |

Conditions at Selected Stages

| Stage Number | 1 | 6 | 15 | 25 |
|---|---|---|---|---|
| Temperature, °F. | 14.8 | 61.9 | 79.5 | 210 |
| Liquid, $CO_2$, Mol % | 95.1 | 39.3 | 25.1 | 1. |
| Liquid, Ethane, Mol % | 4.01 | 4.46 | 18.3 | 13. |
| Liquid, Propane-Plus, Mol % | 0.76 | 56.1 | 56.5 | 85. |
| Liquid, Reduced Temperature | 0.865 | 0.780 | 0.811 | 0. |
| Liquid Flow, Mols/Hr | 2250 | 12173 | 21238 | 1276 |
| Vapor, $CO_2$, Mol % | 93.7 | 86.4 | 63.4 | 3. |
| Vapor, Ethane, Mol % | 5.11 | 5.10 | 24.2 | 30. |

-continued
SIMULATED RUN 2

| | | | | |
|---|---|---|---|---|
| Vapor, Propane-Plus, Mol % | 0.24 | 7.8 | 12.1 | 66. |
| Vapor Flow, Mols/Hr | 3265 | 4930 | 8395 | 1323 |
| Relative Volatility, $CO_2$:Ethane | 0.773 | 1.92 | 1.91 | 1. |

[a] Stages are theoretical stages (trays, partial condensers, reboilers), 100% efficient.
b For full amount of feed, as shown.
c Per 1000 mols/hr. of feed

[d] Pseudo-binary $CO_2$ composition $= \left( \dfrac{CO_2}{CO_2 + \text{ethane}} \right) \times 100$

[e] Mols cited are lb-mols

SIMULATED RUN 3
Summary

| | |
|---|---|
| Feed, Mols[e]/Hr | 1776 |
| Feed $CO_2$, Mol % | 60 |
| Feed Ethane, Mol % | 18 |
| Stages[a], Total | 30 |
| Additive Rate, Mols/Hr | 995 |
| Ethane Recovery in Bottoms Product | 93.5 |
| Ethane, Composition in Overhead, Mol % | 1.8 |
| $CO_2$ Recovery in Overhead, % | 99.0 |
| $H_2S$ Elimination from Overhead, % | 99.8 |
| Additive Loss into Overhead, Mols/Hr | 3.9 |
| "Split", $\dfrac{(CO_2 \text{ Ohd})(\text{Ethane Btm})}{(CO_2 \text{ Btm})(\text{Ethane Ohd})}$ | 1410 |

Column Operating Conditions - 400 psia

| Heating (Cooling) Duty MMBTU/Hr | | Temperature | Location Stage | |
|---|---|---|---|---|
| b | c | | | |
| (3.85) | (2.2) | 16° F. | 1 | Overhead Partial Condenser |
| | | | | Top Section of Column |
| (5.44) | (3.1) | 30° F. | 2 thru 5 | Intermediate Partial Condenser |
| | | | | Additive Added to 6th Stage |
| | | | | Middle Section of Column |
| — | — | 34° F. | 7 thru 16 | Feed Addition |
| | | | | Bottom Section of Column |
| 23.0 | 13.0 | 205° F. | 18 thru 25 | Reboiler |

Material Balance

| | Feed | Additive | $CO_2$ Product Overhead | Ethane-Plus Product Bottoms | |
|---|---|---|---|---|---|
| Mols/Hr $CO_2$ | 1069.0 | 0.0 | 1058.1 | 10.9 | 99.0% Recovery in Overhead |
| Mols/Hr Ethane | 310.0 | 0.0 | 20.0 | 290.0 | 93.5% Recovery in Bottoms |
| Mols/Hr $H_2S$ | 5.0 | 0.0 | 0.0083 | 4.992 | 99.8% Elimin. from Overhead |
| Mols/Hr Propane | 253.0 | 59.7 | 3.2 | 309.5 | |
| Mols/Hr n-Butane | 92.0 | 463.6 | 0.7 | 554.9 | |
| Mols/Hr n-Pentane | 36.0 | 362.1 | 0.0 | 398.1 | |
| Mols/Hr n-hexane | 11.0 | 109.4 | 0.0 | 120.4 | |
| TOTAL | 1776.0 | 994.8 | 1082.0 | 1688.8 | |
| Mol % $CO_2$ | 60.2 | 0.0 | 97.8 | 0.65 | |
| Mol % $C_2$ | 17.5 | 0.0 | 1.8 | 17.2 | |
| Mol % Propane-Plus | 22.1 | 100 | 0.36 | 81.9 | |
| ppm $H_2S$ | 2800 | 0 | 7.7 | 3000 | |
| °F. Temperature | 30.7 | 31.0 | 16.3 | 204.6 | |
| Mol % Liquid | 79.1 | 100.0 | 0.0 | 100.0 | |
| Mol % $CO_2$ (pseudo-bin.[d]) | 77.5 | — | 98.1 | 3.6 | |

Conditions at Selected Stages

| Stage Number | 1 | 6 | 17 | 30 |
|---|---|---|---|---|
| Temperature, °F. | 16.3 | 30.2 | 34.4 | 205.0 |
| Liquid, $CO_2$, Mol % | 97.9 | 65.5 | 51.9 | 0.64 |
| Liquid, Ethane, Mol % | 1.37 | 1.89 | 16.2 | 17.2 |
| Liquid, Propane-Plus, Mol % | 0.76 | 32.6 | 31.7 | 81.9 |
| Liquid, Reduced Temperature | 0.867 | 0.777 | 0.797 | 0.90 |
| Liquid Flow, Mols/Hr | 790 | 3313 | 4758 | 1689 |
| Vapor, $CO_2$, Mol % | 97.8 | 95.7 | 80.1 | 2.60 |
| Vapor, Ethane, Mol % | 1.85 | 1.66 | 14.9 | 41.2 |
| Vapor, Propane-Plus, Mol % | 0.37 | 2.67 | 4.15 | 55.6 |
| Vapor Flow, Mols/Hr | 1082 | 1829 | 3429 | 2874 |

| -continued | | | | |
|---|---|---|---|---|
| SIMULATED RUN 3 | | | | |
| Relative Volatility, $CO_2$:Ethane | 0.740 | 1.66 | 1.68 | 1.68 |

(a) Stages are theoretical stages (trays, partial condensers, reboilers), 100% efficient
b For full amount of feed, as shown.
c Per 1000 mols/hr. of feed (d) Pseudo-binary $CO_2$ composition $= \left( \dfrac{CO_2}{CO_2 + \text{ethane}} \right) \times 100$ (e) Mols cited are lb-mols Since the azeotrope composition is between 65-70% carbon dioxide, the feeds presented in the three simulations of 87%, 63% and 78% (pseudo-binary basis) are on both the high and low sides of the azeotrope composition. The respective bottom products lean in carbon dioxide of 25%, 7% and 4% are significantly lower than the feed composition. The overhead products, rich in carbon dioxide at 95%, 95% and 98%, are significantly richer in carbon dioxide content than the azeotrope composition. Thus, the additive has made possible a more complete separation of carbon dioxide from ethane in all three simulations. A distillation without additive could not have produced such complete separations. Simulation 3 is particularly noteworthy in that the carbon dioxide overhead stream was substantially free of ethane and the ethane bottoms product was substantially free of carbon dioxide. Even more complete separations could be achieved.

The heating and cooling duties are tabulated per 1,000 moles/hour of feed. In this regard, Simulated Run 2 has the least consumption of heating and cooling whereas Simulated Run 3 has the greatest consumption of each.

In regard to the split function, Simulation Run 1 has the least thorough split whereas Simulated Run 3 has the most thorough split.

In general, any material or mixture of materials which causes the relative volatility of an acid gas to a light hydrocarbon from which it is to be separated by distillation to be significantly different than 1 over the range of interest is satisfactory as an agent for this invention. Liquids which are miscible with the acid gas and light hydrocarbon, such as $C_3$-$C_6$ alkanes, are preferred agents because they are typically present in feed mixtures, are easy to separate and recycle, and often have a very beneficial effect in causing the acid gas to be more volatile relative to the light hydrocarbon. Natural gas liquids (NGL) contain such alkanes and can often be separated from bottoms product in conventional separation equipment. Thus, NGL or components thereof can be conveniently recycled to provide agent. It is also clear that materials satisfactory for the agent need not be pure materials. In general, the agent should be liquid at the overhead conditions in the distillation column. It is desirable, of course, to have agents which have volatilities lower than the components to be separated. The agent should also have a freezing point sufficiently low to avoid solids formation in the column.

In addition to the preferred materials mentioned above, there are other classes of materials which meet these requirements. For example, other hydrocarbons such as higher alkanes and naphthenes, halogenated hydrocarbons such as fluoro-chloromethane and fluoro-chloroethane compounds; sulphur dioxide, etc. are believed to be suitable. Those skilled in the art will know, or be able to ascertain using no more than routine experimentation, other suitable agents for use with the invention described herein.

The amount of agent added will be dependent upon factors such as the composition of the feed, operating pressure, throughput of the column, recovery of overhead and bottoms product desired, etc. Such factors can be taken into account by those skilled in the art by determining the operative amounts for any given separation using no more than routine experimentation.

Agent is added to the tower at a point above where feed is introduced since this is where azeotrope formation normally occurs. Although some materials which are suitable agents are contained in the feed in some cases, this alone is not sufficient to prevent azeotrope formation. This is because the agent is usually not sufficiently volatile to rise up the column to the problem area. Thus, even if present in the feed, the agent should be separated and added to a point above the feed.

Although it is possible to add feed at the top of the column, including into the condenser, this is usually not desirable because agent cannot then be separated efficiently from overhead product. Thus, it is preferable to add agent in most cases at a point below the column top to thereby allow separation of additive from the desired overhead product.

In some cases, it is desirable to add agent at more than one column location on a simultaneous basis.

Figure 7:
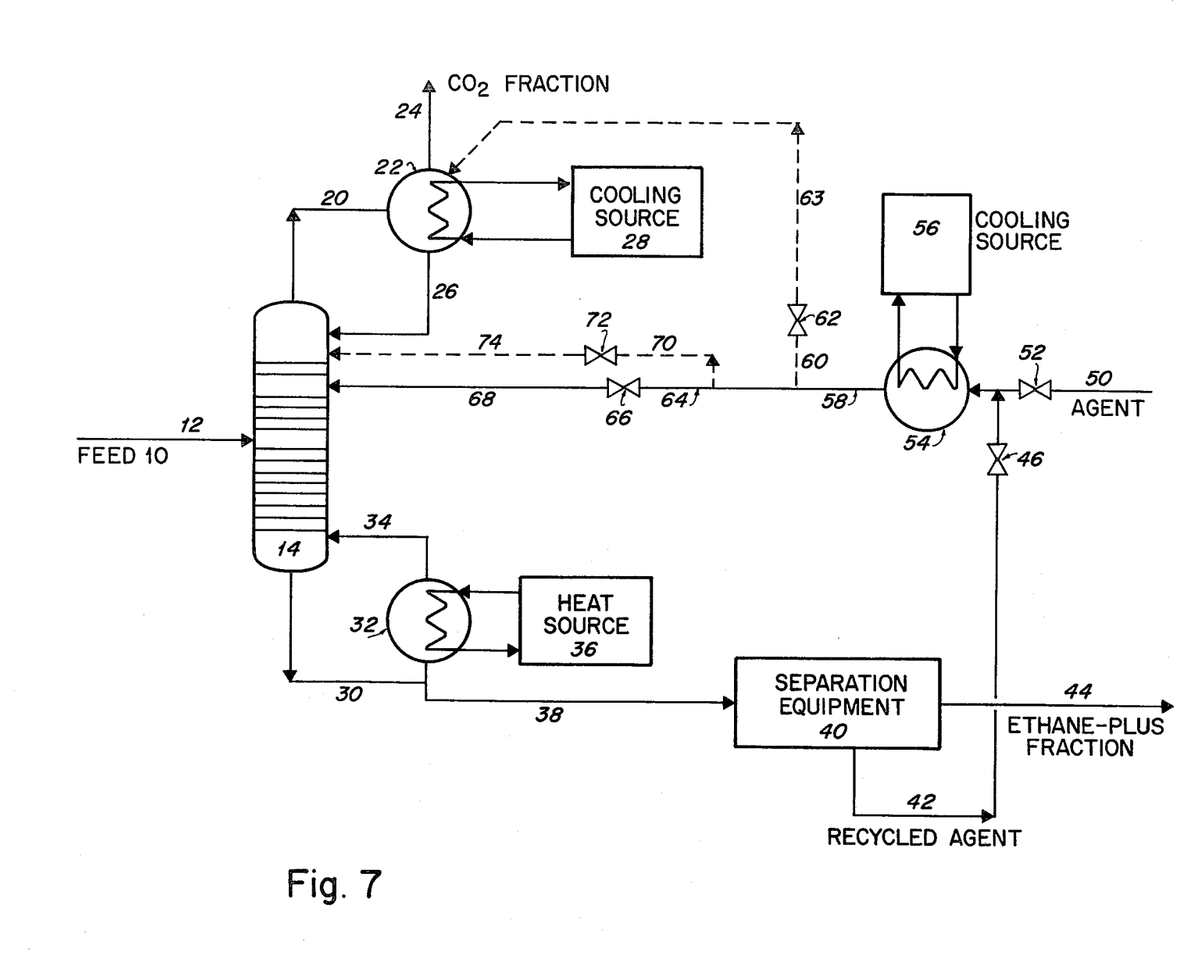
FIG. 7 is a schematic flow diagram illustrating apparatus suitable for carrying out the invention described herein.

An apparatus for carrying out a separation of carbon dioxide from ethane according to this invention is schematically illustrated in FIG. 7. Therein, feed mixture 10, containing a mixture of carbon dioxide and ethane, and usually other components such as heavier hydrocarbons, nitrogen, etc., enters through feed line 12 into distillation column 14. Column 14 contains a number of vapor-liquid contact devices such as trays or packing, with the exact number of contact stages depending upon the required operating conditions.

Overhead stream 20 is rich in carbon dioxide and passes to partial condenser 22 from which the remaining vapor stream 24 exists as carbon dioxide product. This product stream also contains, of course, components present in the feed which are more volatile than carbon dioxide, such as any nitrogen present in the feed. Liquid from the partial condenser returns to column 14 in line 26 where it serves as reflux for tower 14. Condenser 22 is cooled by external cooling source 28.

The bottoms stream exits from the lower portion of column 14 in bottoms line 30 and contains ethane and other less volatile hydrocarbons or other components, and any agent added to prevent azeotrope formation. A portion of the bottoms product is passed through reboiler 32 and back to column 14 in line 34. Reboiler 32 is heated by an external heat source 36.

The bottoms product passes in line 38 to further separation equipment 40, such as another distillation column. Separation equipment 40 is employed to separate out the agent which is recycled in line 42 back to the column. The amount of recycled agent can be controlled by flow control valve 46. An ethane fraction is also separated in equipment 40 and is directed in line 44 to suitable ethane product facilities.

Agent for preventing azeotrope formation may also be added to the system through line 50 and flow control valve 52. Such externally added agent may be used in lieu of recycled agent or in conjunction with recycled agent. In either case, the agent is cooled in heat exchanger 54, cooled by cooling source 56, and directed through flow lines 58 back towards the column 14.

Agent can be added at a number of different locations, either individually or at several locations simultaneously. As illustrated, agent can be directed in line 64 to flow control valve 66 and flow line 68 and introduced directly onto a tray in the upper section of column 14. Similarly, agent can be added to a higher column tray, such as by passing it in line 70 through control valve 72 and line 74. Agent can also be introduced into condenser 22 by directing agent through line 60, flow control valve 62 and line 63. Other suitable points of addition can be determined, of course, for each particular separation being performed.

INDUSTRIAL APPLICABILITY

This invention is useful in the distillative separation of acid gas components from light hydrocarbon components.

EQUIVALENTS

Those skilled in the art will recognize, or be able to determine using no more than routine experimentation, other equivalents to the specific embodiments described herein.

We claim:

1. In a method for the distillative separation in a distillation column of a feed stream comprising carbon dioxide and a light hydrocarbon component in a mixture, to provide a carbon-dioxide-enriched overhead product and a light hydrocarbon-enriched bottoms product, including the operation of a distillation column under conditions of temperature, pressure and composition sufficient to form a binary azeotrope between the carbon dioxide and a light hydrocarbon component, which azeotrope limits the concentration of the carbon dioxide in the overhead product withdrawn from said column, the improvement which comprises:

adding to the upper portion of the distillation column and above the point of introduction of the feed stream, a liquid agent which significantly alters the relative volatility between said carbon dioxide and said light hydrocarbon component and prevents the azeotrope formation therebetween, the liquid agent added in an amount of greater than about 10 mol percent based on the mols of liquids in the column at or below the point of introduction of the liquid agent and sufficient to provide a relative volatility of greater than one of the said carbon dioxide to the said light hydrocarbon component at or below the point of introduction of the liquid agent, which provides a carbon-dioxide-enriched overhead product having a carbon dioxide concentration greater than the carbon dioxide concentration of the binary azeotrope.

2. The method of claim 1 wherein said agent comprises a $C_3$–$C_6$ alkane or a mixture of $C_3$–$C_6$ alkanes.

3. The method of claim 1 wherein said agent is separated from bottoms product from said distillation column and recycled to said column.

4. The method of claim 1 wherein said light hydrocarbon is ethane.

5. The method of claim 1 wherein said light hydrocarbon is ethylene.

6. The method of claim 1 wherein said agent is miscible with the carbon dioxide and light hydrocarbon liquid phase.

7. The method of claim 6 wherein said agent comprises at least one $C_3$–$C_6$ alkane.

8. The method of claim 1 wherein said agent comprises n-butane.

9. The method of claim 1 wherein the concentration of carbon dioxide in the carbon-dioxide-enriched overhead product is significantly greater than two-thirds carbon dioxide.

10. The method of claim 1 which includes withdrawing the agent from said column with the bottom stream, separating the agent from the bottom stream and recycling at least a part of the separated agent to said column.

11. The method of claim 1 wherein the feed stream comprises natural gas which contains butane, and which method includes:
a. separating the butane from the light hydrocarbon-enriched bottoms product; and
b. introducing the separated butane in liquid form into the column as said liquid agent.

12. The method of claim 1 wherein the feed stream comprises ethane and the carbon-dioxide-enriched overhead product is substantially free of ethane, and the light hydrocarbon-enriched bottoms product is substantially free of carbon dioxide.

13. The method of claim 1 which includes:
(a) withdrawing from the column and at least partially condensing the carbon-dioxide-enriched overhead product, to provide an enriched carbon dioxide product stream and a condensed liquid stream;
(b) recycling the condensed stream to the column as a reflux stream;
(c) withdrawing from the column and separating from the light hydrocarbon-enriched bottoms product said agent stream and an ethane-plus stream;
(d) cooling the said separated agent stream;
(e) recycling the cooled separated agent stream back to the column above the point of introduction of the feed stream; and,
(f) withdrawing the separated ethane-plus stream.

14. The method of claim 13 which includes:
a. reboiling a portion of the withdrawn light hydrocarbon-enriched product; and
b. recycling the reboiled product back into the lower portion of the said distillation column.

15. The method of claim 13 which includes:
a. introducing and condensing an addition agent in the condensing step; and
b. introducing the added condensed agent and the recycled condensed agent into the distillation column.

16. The method of claim 1 wherein the liquid agent is present in a concentration of about 30 to 50 mol percent of the liquids in the column and about 70 to 90 mol percent in the bottoms product.

17. The method of claim 1 wherein the amount of liquid agent in the column at or below the point of introduction of the liquid agent into the column is greater than about 25 mol percent in the liquids in the column.

18. A method for separating carbon dioxide from a feed-stream mixture containing carbon dioxide and ethane, comprising:
  (a) introducing said mixture into a distillation column containing a plurality of vapor-liquid contact devices;
  (b) operating said distillation column at conditions of pressure, temperature and composition sufficient to produce an enriched carbon dioxide overhead stream and an enriched ethane bottom stream, said conditions of temperature, pressure and composition also being sufficient normally for the formation of a carbon dioxide/ethane azeotrope which would limit the concentration of carbon dioxide in said overhead stream to the azeotropic concentration, based upon a binary mixture of carbon dioxide and ethane; and,
  (c) introducing into the upper portion of said distillation column and above the point of introduction of the feed stream a $C_3$–$C_6$ alkane or mixture of alkanes as a liquid agent which is miscible with the carbon dioxide and the ethane, and which liquid agent is added in an amount of greater than about 20 mol percent in the liquids based on the mols of column at or below the point of introduction of the liquid agent and sufficient to provide a relative volatility of greater than one of the carbon dioxide to the ethane at or below the point of introduction of the liquid agent, to provide a carbon-dioxide-enriched overhead stream having a carbon dioxide concentration greater than the carbon dioxide concentration of the binary carbon dioxide/ethane azeotrope.

19. The method of claim 18 wherein the liquid agent is present in a concentration of about 30 to 50 mol percent of the liquids in the column and about 70 to 90 mol percent in the bottoms product.

20. The method of claim 18 wherein said agent comprises n-butane.

21. The method of claim 18 wherein said agent is separated from bottoms product from said distillation column and recycled to said column.

22. The method of claim 18 wherein the relative volatility of the carbon dioxide to the ethane is about 1.65 or greater.

23. The method of claim 18 wherein the amount of liquid agent in the column at or below the point of introduction of the liquid agent into the column is greater than about 30 mol percent in the liquids in the column.

24. The method of claim 18 wherein the carbon-dioxide-enriched overhead product is substantially free of ethane and the ethane-enriched bottoms product is substantially free of carbon dioxide.

* * * * *